(12) United States Patent
Chen (10) Patent No.: US 11,313,849 B2
(45) Date of Patent: Apr. 26, 2022

(54) EXPANSION RATIO DETECTION SYSTEM

(71) Applicant: KAUO JEI IND CO., LTD., New Taipei (TW)

(72) Inventor: Wen-Ho Chen, New Taipei (TW)

(73) Assignee: KAUO JEI IND CO., LTD., New Taipei (TW)

( * ) Notice: Subject to any disclaimer, the term of this patent is extended or adjusted under 35 U.S.C. 154(b) by 290 days.

(21) Appl. No.: 16/565,490

(22) Filed: Sep. 10, 2019

(65) Prior Publication Data
US 2021/0072218 A1   Mar. 11, 2021

(51) Int. Cl.
*G01N 33/44* (2006.01)
*B29C 43/24* (2006.01)
*G01K 5/00* (2006.01)
*B29C 44/60* (2006.01)

(52) U.S. Cl.
CPC ............ *G01N 33/445* (2013.01); *B29C 43/24* (2013.01); *G01K 5/00* (2013.01); *B29C 44/60* (2013.01); *B29C 2791/003* (2013.01)

(58) Field of Classification Search
CPC ................................ G01N 33/445; G01K 5/00
See application file for complete search history.

(56) References Cited

U.S. PATENT DOCUMENTS

| 3,693,421 | A | * | 9/1972 | Karper | G01N 33/445 |
| | | | | | 73/843 |
| 3,847,018 | A | * | 11/1974 | Aston | G01N 3/14 |
| | | | | | 73/818 |
| 7,320,242 | B2 | * | 1/2008 | Hoo Fatt | G01N 3/30 |
| | | | | | 73/12.14 |

FOREIGN PATENT DOCUMENTS

| CN | 106802263 | * | 6/2017 |
| CN | 207908410 U | * | 9/2018 |
| CN | 110103383 | * | 8/2019 |
| FR | 2423785 | * | 11/1979 |
| JP | 4-249756 | * | 9/1992 |
| JP | 2011-214978 | * | 10/2011 |

* cited by examiner

*Primary Examiner* — Daniel S Larkin
(74) *Attorney, Agent, or Firm* — Chun-Ming Shih; HDLS IPR Services (57) ABSTRACT

An expansion ratio detection system for rubber, including a controller, a rubber sampling module, a rubber calender, a temperature control module, and an expansion ratio detection module. The rubber sampling module obtains a rubber to be tested consistent with a weight value. After the temperature control module determines that the rubber to be tested has reached a first temperature value, the rubber calender outputs the rubber to be tested having a thickness value. The expansion ratio detection module obtains an expansion ratio according to twice the thickness value and a roller pitch.

10 Claims, 5 Drawing Sheets

EXPANSION RATIO DETECTION SYSTEM

BACKGROUND

Technical Field

The present disclosure relates to an expansion ratio detection system, and more particularly to an expansion ratio detection system for rubber processing.

Description of Related Art

The statements in this section merely provide background information related to the present disclosure and do not necessarily constitute prior art.

In the field of rubber testing, such as the national standard of the People's Republic of China (GB), the International Organization for Standardization (ISO), the American Society for Testing and Materials (ASTM), and Rubber Research Institute of Malaysia (RRIM), outside of North America, ISO standards have gradually become popular.

However, in the field of rubber testing, there is still a lack of a one-stop system for rapid and continuous detection of rubber. Moreover, when rubber is actually produced and applied to a commercial production line, since a roller pitch of a rubber calender and a temperature of a rubber to be tested cannot be accurately controlled according to the rubber to be tested having a specific sampling weight, accurate expansion ratio cannot be obtained. This has caused problems for rubber testing companies and rubber-related manufacturers, and increased production costs.

Therefore, how to design an expansion ratio detection system to solve the technical problems above is an important subject studied by the inventors and proposed in the present disclosure.

SUMMARY

The purpose of the present disclosure is to provide an expansion ratio detection system, which can accurately control a roller pitch of a rubber calender and a temperature value of a rubber to be tested according to the rubber to be tested having a specific sampling weight, thereby obtaining an accurate expansion ratio; and to achieve the purpose of reducing the production costs of rubber-related manufacturing.

In order to achieve the purpose above-mentioned, the expansion ratio detection system for a rubber continuously calendered at least six times and has a mooney index, including a controller, a rubber sampling module, a rubber calender, a temperature control module and an expansion ratio detection module. The controller produces a weight value, a first temperature value and a roller pitch G. A rubber sampling module is coupled to the controller, and the rubber sampling module samples the rubber according to the weight value to obtain a rubber to be tested consistent with the weight value. A rubber calender is coupled to the controller and the rubber sampling module, and the rubber calender includes two rollers arranged in parallel, the two rollers are spaced apart from each other by the roller pitch G. A temperature control module is coupled to the controller and the rubber calender, the temperature control module maintains the rubber to be tested to have the first temperature value, when the temperature control module determines that the rubber to be tested in the rubber calender has reached the first temperature value, the two rollers continuously calender the rubber to be tested at least two times, and the rubber calender outputs the rubber to be tested having a thickness value D. An expansion ratio detection module coupled to the controller and the rubber calender, the expansion ratio detection module obtains an expansion ratio $E=2D/G$ according to twice the thickness value D and the roller pitch G. The mooney index is a mooney viscosity between 61.07 and 91.06, the roller pitch G is changed in a minimum unit of 0.001 mm depending on number of rollings of the rubber, and the roller pitch G is between 0.065 mm and 0.145 mm.

In one embodiment, the weight value is 25 grams.

In one embodiment, the first temperature value is 25 degrees Celsius.

In one embodiment, the number of rollings of the rubber is six times, and the roller pitch is 0.065 mm.

In one embodiment, the expansion ratio detection system further includes a plasticity detection module, the plasticity detection module folds the rubber to be tested that has been continuously calendered twice, and cuts out a cylinder having a thickness with twice the thickness value D, and then, the plasticity detection module heats the cylinder to a second temperature value, and the plasticity detection module applies a pressure of 10 kg to the cylinder and releases the cylinder after maintaining the pressure of 10 kg for 15 seconds, the plasticity detection module obtains a first rebound thickness of the cylinder after first impact and rebound moment for the cylinder, and the plasticity detection module outputs an initial plasticity value, the first rebound thickness has a minimum unit of 0.01 mm.

In one embodiment, the second temperature value is 100 degrees Celsius.

In one embodiment, the expansion ratio detection system further includes a plasticity detection module, the plasticity detection module folds the rubber to be tested that has been continuously calendered twice, and cuts out a cylinder having a thickness with twice the thickness value D, and then, the cylinder is heated to 140 degrees Celsius and cooled the cylinder after maintained 140 degrees Celsius for 30 minutes, finally, the plasticity detection module heats the cylinder to a second temperature value, and the plasticity detection module applies a pressure of 10 kg to the cylinder and releases the cylinder after maintaining for 15 seconds, the plasticity detection module obtains a first rebound thickness of the cylinder after first impact and rebound moment for the cylinder, and the plasticity detection module outputs an initial plasticity value, the first rebound thickness has a minimum unit of 0.01 mm.

In one embodiment, the second temperature value is 100 degrees Celsius.

In one embodiment, a speed ratio of the two rollers is 1:1.

In one embodiment, the temperature control module is a water-cooled chiller.

When operating the expansion ratio detection system, the controller causes the rubber sampling module to obtain the rubber to be tested according to the weight value. Afterward, the temperature control module maintaining the rubber to be tested to have the first temperature value. When the temperature control module determines that the rubber to be tested in the rubber calender has reached the first temperature value, the two rollers spaced apart from each other by the roller pitch G are continuously calendered twice for the rubber to be tested, and the rubber calender outputs the rubber to be tested having the thickness value D. Finally, the expansion ratio detection module obtains the expansion ratio $E=2D/G$ according to twice the thickness value D and the roller pitch G. To this end, the present disclosure can accurately control the roller pitch G of the rubber calender and the temperature value of the rubber to be tested (the roller pitch G is changed in a minimum unit of 0.001 mm depending on number of rollings of the rubber), thereby obtaining an accurate expansion ratio E and achieving the purpose to reduce the production cost of the rubber-related manufacturing industry.

In order to further understand the techniques, means, and effects of the present disclosure for achieving the intended purpose. Please refer to the following detailed description and drawings of the present disclosure. The drawings are provided for reference and description only, and are not intended to limit the present disclosure.

DETAILED DESCRIPTION

The embodiments of the present disclosure are described by way of specific examples, and those skilled in the art can readily appreciate the other advantages and functions of the present disclosure. The present disclosure may be embodied or applied in various other specific embodiments, and various modifications and changes can be made without departing from the spirit and scope of the present disclosure.

It should be understood that the structures, the proportions, the sizes, the number of components, and the like in the drawings are only used to cope with the contents disclosed in the specification for understanding and reading by those skilled in the art, and it is not intended to limit the conditions that can be implemented in the present disclosure, and thus is not technically significant. Any modification of the structure, the change of the proportional relationship, or the adjustment of the size, should be within the scope of the technical contents disclosed by the present disclosure without affecting the effects and the achievable effects of the present disclosure.

The technical content and detailed description of the present disclosure will be described below in conjunction with the drawings.

Figure 1:
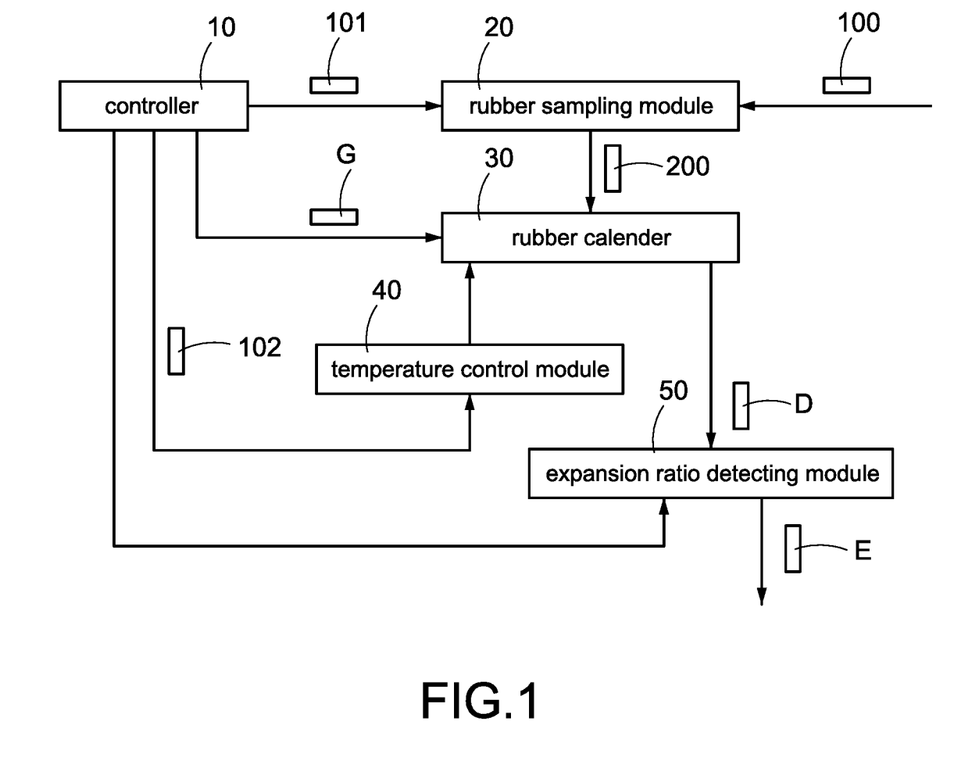
FIG. 1 is an architectural diagram of a first embodiment of an expansion ratio detection system of the present disclosure.

Please refer to FIG. 1, which shows an architectural diagram of a first embodiment of an expansion ratio detection system of the present disclosure.

The expansion ratio detection system of the present disclosure is applied to a rubber 100 continuously calendered at least six times and has a mooney index, including a controller 10, a rubber sampling module 20, a rubber calender 30, a temperature control module 40 and an expansion ratio detection module 50. The mooney index is a mooney viscosity between 61.07 and 91.06. The mooney viscosity is a comprehensive index of hardness, viscosity, and flow rate of natural rubber. The higher value of the mooney viscosity means harder, less sticky, poor fluidity and low plasticity. On the contrary, the lower value of the mooney viscosity means softer, more sticky, better fluidity and higher plasticity.

The controller 10 produces a weight value 101, a first temperature value 102 and a roller pitch G. The controller 10 may be any of a CPU, an MPU, an ASIC, or a SoC.

A rubber sampling module 20 is coupled to the controller 10, and the rubber sampling module 20 samples the rubber 100 according to the weight value 101 to obtain a rubber to be tested 200 consistent with the weight value 101. The rubber sampling module 20 may be a device consisting of a robot arm, a cutter, and a conveyor belt. In the first embodiment of the present disclosure, the weight value 101 is 25 grams.

The rubber calender 30 is coupled to the controller 10 and the rubber sampling module 20, and the rubber calender 30 includes two rollers (not shown in FIGs.) arranged in parallel, the two rollers are spaced apart from each other by the roller pitch G. The roller pitch G is changed in a minimum unit of 0.001 mm depending on number of rollings of the rubber (the number of rollings of the rubber is at least six times), and the roller pitch G is between 0.065 mm and 0.145 mm. In the first embodiment of the present disclosure, the number of rollings of the rubber is six times, the roller pitch G is 0.065 mm, and the optimum speed ratio of the two rollers is 1:1.

The temperature control module 40 is coupled to the controller 10 and the rubber calender 30, and the temperature control module 40 maintains the rubber to be tested 200 to have a first temperature value 102. When the temperature control module 40 determines that the rubber to be tested 200 in the rubber calender has reached the first temperature value 102, the two rollers continuously calender the rubber to be tested 200 at least two times (including continuous rolling of rubber 100 at least six times, the cumulative number of rolling of the same material is at least eight times), and the rubber calender 30 outputs the rubber to be tested 200 having a thickness value D. In a first embodiment of the present disclosure, the first temperature value 102 is 25 degrees Celsius. In the first embodiment of the present disclosure, the temperature control module 40 is a water-cooled chiller.

The expansion ratio detection module 50 is coupled to the controller 10 and the rubber calender 30. The expansion ratio detection module 50 obtains an expansion ratio E=2D/G according to twice the thickness value D and the roller pitch G. In other words, the expansion ratio detection module 50 may determine the difference in expansion ratio between different test procedures by the thickness value D measured and the roller pitch G corresponding to the number of rolling times of the rubber 100 used at the beginning (for example, the number of rolling times of the rubber 100 is six times, the roller pitch G is 0.065 mm). By comparing different rubber grades or different rubber types used in each test, rubber testers and rubber-related manufacturers may easily control material and cost by expansion rate loss caused by processing factors such as calendering or heat treatment.

Figure 2:
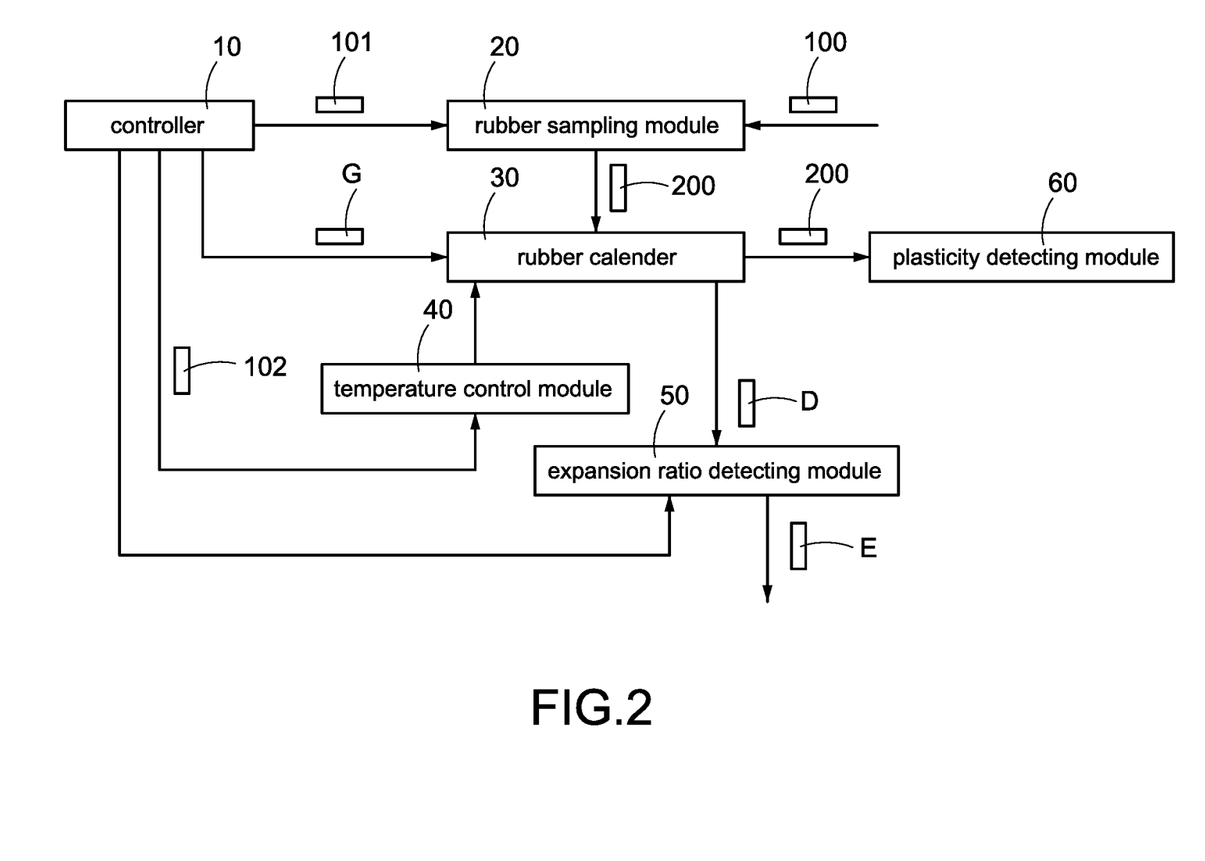
FIG. 2 is an architectural diagram of a second embodiment of the expansion ratio detection system of the present disclosure.
Figure 3A:
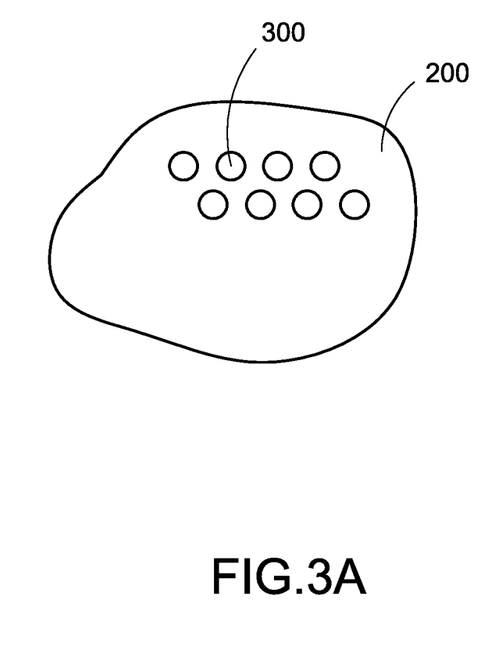
FIGS. 3A, 3B are architectural diagrams of a cylinder cut out by a plasticity detection module of the present disclosure.
Figure 3B:
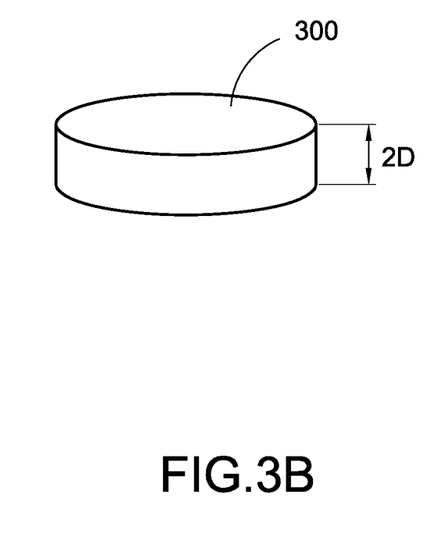
Figure 4:
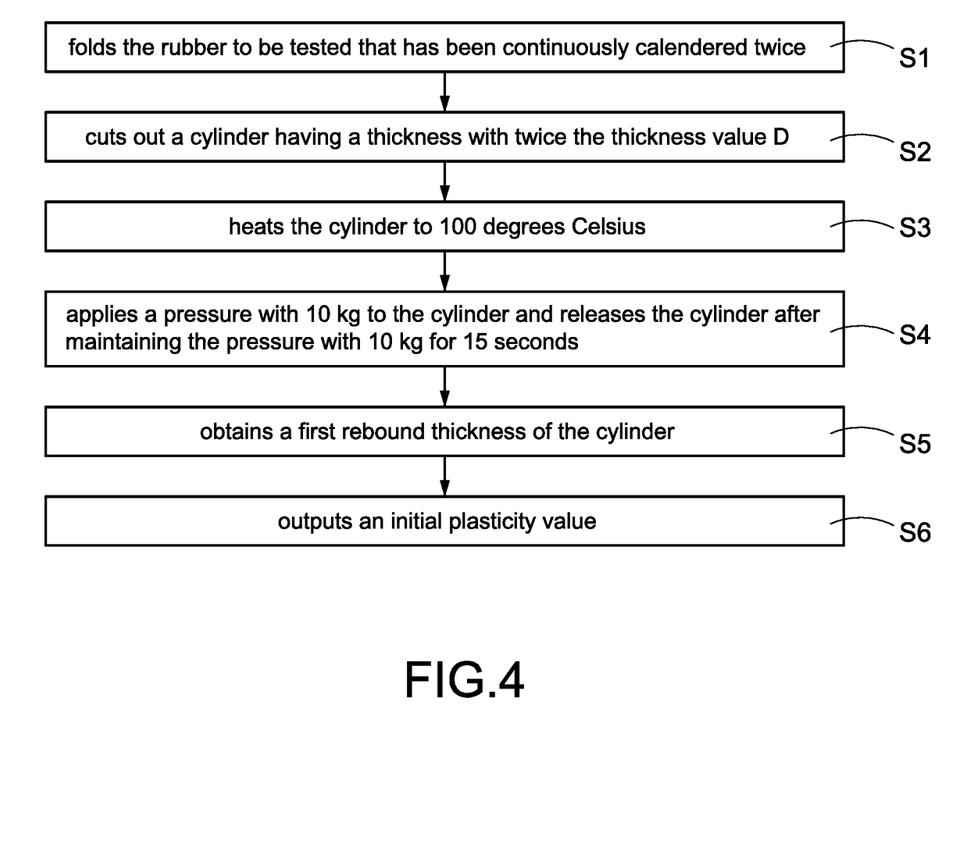
FIG. 4 is a flowchart showing outputting an initial plasticity value of the expansion ratio detection system of the present disclosure.

Please refer to FIG. 2 to FIG. 4. FIG. 2 is an architectural diagram of a second embodiment of the expansion ratio detection system of the present disclosure. FIG. 3A and FIG. 3B are architectural diagrams of a cylinder cut out by a plasticity detection module of the present disclosure. FIG. 4 is a flowchart showing outputting an initial plasticity value of the expansion ratio detection system of the present disclosure.

The second embodiment of the present disclosure is substantially the same as the first embodiment, but the second embodiment further includes a plasticity detection module 60. The plasticity detection module 60 folds the rubber to be tested 200 that has been continuously calendered twice (as shown in step S1 of FIG. 4), and cuts out a cylinder 300 (step S2 of FIG. 4) having a thickness with twice the thickness value D (that is, 2D, as shown in FIG. 3A and FIG. 3B). Afterward, the plasticity detection module 60 heats the cylinder 300 to a second temperature value (step S3 of FIG. 4), and the plasticity detection module 60 applies a pressure of 10 kg to the cylinder 300 and releases the cylinder 300 after maintaining the pressure of 10 kg for 15 seconds (step S4 of FIG. 4). The second temperature value is 100 degrees Celsius. The plasticity detection module 60 obtains a first rebound thickness of the cylinder 300 after first impact and rebound moment for the cylinder 300 (step S5 of FIG. 4), and the plasticity detection module 60 outputs an initial plasticity value $P_0$ (step S6 of FIG. 4). The first rebound thickness has a minimum unit of 0.01 mm.

Figure 5:
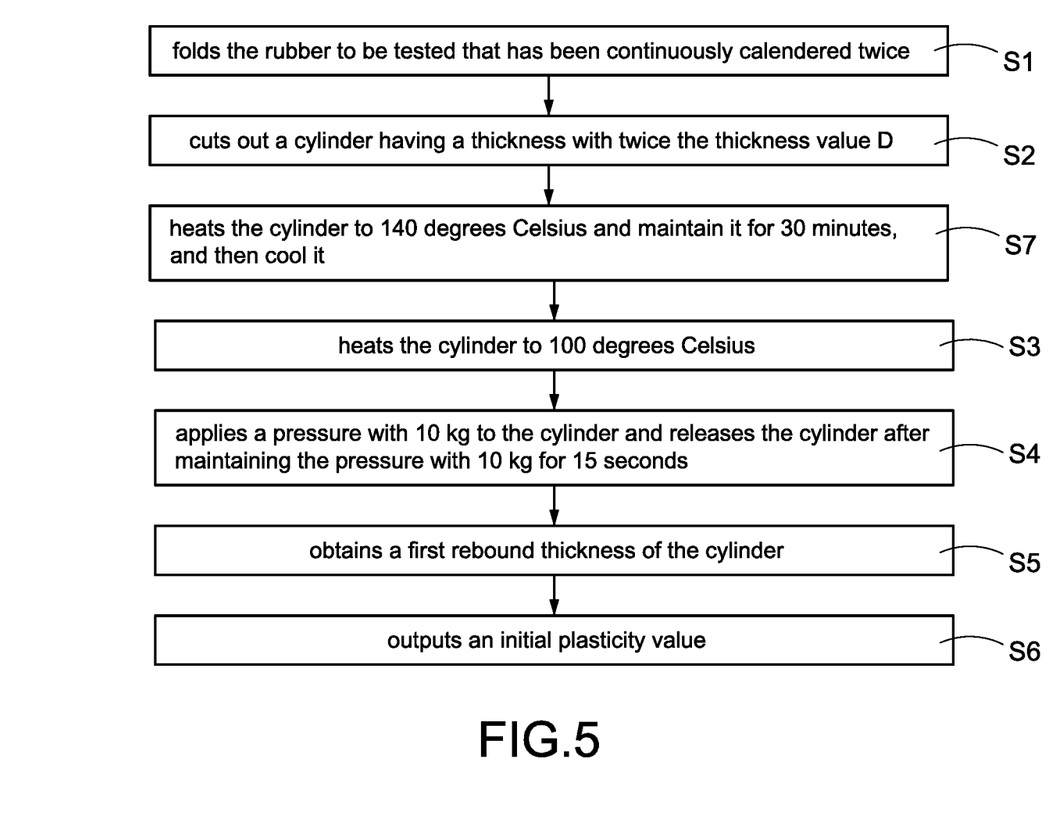
FIG. 5 is a flowchart showing outputting an aging plasticity value of the expansion ratio detection system of the present disclosure.

FIG. 5 is a flowchart showing outputting an aging plasticity value of the expansion ratio detection system of the present disclosure. It is based on the second embodiment of the present disclosure, and is substantially the same as the flow of outputting the initial plasticity value $P_0$, but further includes a step S7 between the foregoing steps S2 and S3. The step S7 is to heat the cylinder 300 to 140 degrees Celsius and maintain the cylinder 300 for 30 minutes, and then cool the cylinder 300 to perform heat aging treatment on the cylinder 300 to obtain an aging plasticity value $P_{30}$.

Further, a plasticity retention index (PRI) may be obtained by the initial plasticity value $P_0$ and the aging plasticity value $P_{30}$ obtained as described above:

$$PRI = \frac{P_{30}}{P_0} \times 100\%$$

When operating the expansion ratio detection system, the controller 10 causes the rubber sampling module 20 to obtain the rubber to be tested 200 according to the weight value 101. Afterward, the temperature control module 40 maintaining the rubber to be tested 200 to have the first temperature value 102. When the temperature control module 40 determines that the rubber to be tested 200 in the rubber calender 30 has reached the first temperature value 102, two rollers spaced apart from each other by the roller pitch G are continuously calendered twice for the rubber to be tested 200, and the rubber calender 30 outputs the rubber to be tested 200 having the thickness value D. Finally, the expansion ratio detection module 50 obtains the expansion ratio E=2D/G according to twice the thickness value D and the roller pitch G. To this end, the present disclosure may accurately control the roller pitch G of the rubber calender (the roller pitch G is changed in a minimum unit of 0.001 mm depending on number of rollings of the rubber) and the temperature value (as 25 degrees Celsius) of the rubber to be tested 200, thereby obtaining an accurate expansion ratio E. Moreover, the expansion ratio E may be numerically compared with the initial plasticity value $P_0$, the aging plasticity value $P_{30}$ and the plasticity residual rate PRI.

When the number of rollings of the rubber 100 is six times, the roller pitch G is 0.065 mm. When the number of rollings of the rubber 100 is ten times, the roller pitch G is 0.075 mm. When the number of rollings of the rubber 100 is sixteen times, the roller pitch G is 0.085 mm. When the number of rollings of the rubber 100 is twenty-two times, the roller pitch G is 0.095 mm. When the number of rollings of the rubber 100 is twenty-eight times, the roller pitch G is 0.125 mm. When the number of rollings of the rubber 100 is thirty-four times, the roller pitch G is 0.145 mm. However, the present disclosure is not limited thereto.

Please refer to a table below.

|  | $P_0$ | $P_{30}$ | PRI | G | mooney | specific gravity | power | expansion rate |
|---|---|---|---|---|---|---|---|---|
| the rubber to be tested A calendering 6 times | 45.0 | 29.2 | 64.89 | 0.0650 | 91.06 | 0.919 | 0.3259 | 52.31 |
| the rubber to be tested A calendering 10 times | 40.0 | 27.0 | 67.50 | 0.0750 | 84.72 | N/A | 0.4355 | 45.33 |
| the rubber to be tested A calendering 16 times | 38.6 | 26.9 | 69.69 | 0.0850 | 80.43 | N/A | 0.6762 | 40.00 |
| the rubber to be tested A calendering 22 times | 37.4 | 28.3 | 75.67 | 0.0950 | 76.00 | 0.920 | 0.8985 | 35.79 |
| the rubber to be tested A calendering 28 times | 32.6 | 25.7 | 78.83 | 0.1250 | 66.62 | 0.920 | 1.1392 | 27.20 |
| the rubber to be tested A calendering 34 times | 31.4 | 24.0 | 76.43 | 0.1450 | 62.25 | 0.920 | 1.3652 | 23.45 |
| the rubber to be tested B calendering 6 times | 37.6 | 26.6 | 70.74 | 0.0500 | 78.18 | N/A | 0.3110 | 68.00 |
| the rubber to be tested B calendering 10 times | 36.6 | 26.1 | 71.31 | 0.0625 | 73.14 | 0.9149 | 0.4150 | 54.40 |
| the rubber to be tested B calendering 16 times | 34.3 | 24.7 | 72.01 | 0.0800 | 67.66 | N/A | 0.6340 | 42.50 |
| the rubber to be tested B calendering 22 times | 31.9 | 23.1 | 72.54 | 0.1150 | 61.07 | N/A | 0.8520 | 29.57 |

Please refer to another table below

| | $P_0$ | $P_{30}$ | PRI | G | mooney | specific gravity | power | expansion rate |
|---|---|---|---|---|---|---|---|---|
| C company's rubber C1 | 32.5 | 19.7 | 60.62 | 0.100 | 65.72 | 0.9143 | 0.2340 | 34.00 |
| C company's rubber C2 | 32.7 | 19.9 | 60.86 | 0.100 | 65.81 | 0.9150 | 0.2345 | 34.00 |
| D company's rubber D1 | 32.5 | 18.1 | 55.69 | 0.130 | 63.38 | 0.9127 | 0.2520 | 26.15 |
| D company's rubber D2 | 30.2 | 17.7 | 58.61 | 0.130 | 61.41 | 0.9128 | 0.2441 | 26.15 |
| D company's rubber D3 | 32.4 | 18.7 | 57.72 | 0.130 | 64.74 | 0.9122 | 0.2542 | 26.15 |
| D company's rubber D4 | 30.2 | 16.7 | 55.30 | 0.130 | 60.51 | 0.9126 | 0.2462 | 26.15 |

It may be seen from the above tables above with the average specific gravity, the rubber of D company is higher than that of C company. However, with the average expansion ratio, the rubber of D company is lower than that of C company. Representing D company's rubber may be maliciously doped.

Further, since the rubber trading market is trading and processing in a relatively large order of magnitude, it is important to accurately estimate the production cost of the rubber-related industry (such as the tire industry, medical rubber or daily necessities, etc.) for the expansion ratio E. The present disclosure may help rubber testers and rubber-related manufacturers to know the difference in expansion ratio between different test procedures, and by comparing different rubber grades or different rubber types used in each test, rubber testers and rubber-related manufacturers may easily control material and cost by expansion rate loss caused by processing factors such as calendering or heat treatment.

The present disclosure may control an access authority of the expansion ratio E by combination with RFID, fingerprint, voiceprint, face recognition, etc. However, the present disclosure is not limited thereto.

The rubber industry knows that the closer to the equator, the higher the average natural rubber production capacity, the better the average quality and the thicker the secreted gum. The above-mentioned technology has accumulated many years of experience and research and development design, and can be a calculation model and testing equipment for natural rubber, which can test and calculate the loss of specific gravity, loss of rubber expansion rate, loss of power consumption, manpower and machine wear. It is possible to calculate the misunderstanding of the price and value of the natural rubber of various grades and numbers, and can analyze the comparative data of the price and value of the natural rubber. From then on, it can be avoided to the greatest extent that the label of the natural rubber is incorrect, or because the lack of correct data, the procurement personnel only purchase according to their rules of thumb or market conditions, or human error, resulting in invisible losses. Especially for companies with a large amount of natural rubber, the use of the aforementioned technology will certainly reduce the cost of raw material procurement, or increase the production cost due to non-optimal specifications, and also avoid the mistakes of the procurement staff or the opaque zone. It saves a lot of money and avoids the waste of global resources for the human, tire and natural rubber industries.

The above is only a detailed description and drawings of the preferred embodiments of the present disclosure, but the features of the present disclosure are not limited thereto, and are not intended to limit the present disclosure. All the scope of the present disclosure shall be subject to the scope of the following claims. The embodiments of the spirit of the present disclosure and its similar variations are intended to be included in the scope of the present disclosure. Any variation or modification that can be easily conceived by those skilled in the art in the field of the present disclosure can be covered by the following claims.

What is claimed is:

1. An expansion ratio detection system for a rubber calendered and having a mooney index, comprising:
    a controller configured to produce a weight value, a first temperature value and a roller pitch G,
    a rubber sampling module coupled to the controller, and the rubber sampling module configured to sample the rubber according to the weight value to obtain a rubber to be tested consistent with the weight value,
    a rubber calender coupled to the controller and the rubber sampling module, the rubber calender including two rollers arranged in parallel, the two rollers spaced apart from each other by the roller pitch G,
    a temperature control module coupled to the controller and the rubber calender, the temperature control module configured to maintain the rubber to be tested to have the first temperature value, when the temperature control module configured to determine that the rubber to be tested in the rubber calender has reached the first temperature value, the two rollers configured to calender the rubber to be tested, and the rubber calender configured to output the rubber to be tested having a thickness value D, and
    an expansion ratio detection module coupled to the controller and the rubber calender, the expansion ratio detection module configured to obtain an expansion ratio E=2D/G according to twice the thickness value D and the roller pitch G,
    wherein the mooney index is a mooney viscosity between 61.07 and 91.06, the roller pitch G is changed in a minimum unit of 0.001 mm depending on number of rollings of the rubber, and the roller pitch G is between 0.065 mm and 0.145 mm.

2. The expansion ratio detection system in claim 1, wherein the weight value is 25 grams.

3. The expansion ratio detection system in claim 1, wherein the first temperature value is 25 degrees Celsius.

4. The expansion ratio detection system in claim 1, wherein the roller pitch is 0.065 mm.

5. The expansion ratio detection system in claim 1, further comprising a plasticity detection module, the plasticity detection module configured to fold the rubber to be tested that has been continuously calendered twice, and configured to cut out a cylinder having a thickness with twice the thickness value D, and then, the plasticity detection module configured to heat the cylinder to a second temperature value, and the plasticity detection module configured to apply a pressure of 10 kg to the cylinder and release the cylinder after maintaining the pressure of 10 kg for 15 seconds, the plasticity detection module configured to obtain a first rebound thickness of the cylinder after first impact and rebound moment for the cylinder, and the plasticity detection module configured to output an initial plasticity value, wherein the first rebound thickness has a minimum unit of 0.01 mm.

6. The expansion ratio detection system in claim 5, wherein the second temperature value is 100 degrees Celsius.

7. The expansion ratio detection system in claim 1, further comprising a plasticity detection module, the plasticity detection module configured to fold the rubber to be tested that has been continuously calendered twice, and cut out a cylinder having a thickness with twice the thickness value D, and then, the cylinder being heated to 140 degrees Celsius and being cooled after the cylinder being maintained at 140 degrees Celsius for 30 minutes, finally, the plasticity detection module configured to heat the cylinder to a second temperature value, and the plasticity detection module configured to apply a pressure of 10 kg to the cylinder and release the cylinder after maintaining for 15 seconds, the plasticity detection module configured to obtain a first rebound thickness of the cylinder after first impact and rebound moment for the cylinder, and the plasticity detection module configured to output an initial plasticity value, wherein the first rebound thickness has a minimum unit of 0.01 mm.

8. The expansion ratio detection system in claim 7, wherein the second temperature value is 100 degrees Celsius.

9. The expansion ratio detection system in claim 1, wherein a speed ratio of the two rollers is 1:1.

10. The expansion ratio detection system in claim 1, wherein the temperature control module is a water-cooled chiller.

* * * * *